United States Patent [19]

Khalil et al.

[11] Patent Number: 5,198,368
[45] Date of Patent: Mar. 30, 1993

[54] METHODS FOR PERFORMING A SOLID-PHASE IMMUNOASSAY

[75] Inventors: Omar S. Khalil; Charles F. Hanna, both of Libertyville; Thomas F. Zurek, River Forest, all of Ill.

[73] Assignee: Abbott Laboratories, North Chicago, Ill.

[21] Appl. No.: 643,596

[22] Filed: Jan. 18, 1991

Related U.S. Application Data

[62] Division of Ser. No. 184,726, Apr. 22, 1988.

[51] Int. Cl.$^5$ .................. G01N 33/543; G01N 33/546
[52] U.S. Cl. ........................... 436/518; 422/56; 422/58; 435/810; 436/527; 436/528; 436/178; 436/180; 436/805; 436/807; 436/809; 436/810
[58] Field of Search ...................... 422/56, 58, 101; 435/810; 436/527, 528, 178, 180, 518, 805, 807, 809, 810

[56] References Cited

U.S. PATENT DOCUMENTS

| 4,552,839 | 11/1985 | Gould et al. | 435/7 |
|---|---|---|---|
| 4,623,461 | 11/1986 | Hossom et al. | |
| 4,632,901 | 12/1986 | Valkirs et al. | 435/5 |
| 4,652,533 | 3/1987 | Jolley | |
| 4,738,823 | 4/1988 | Engelmann | 422/56 |
| 4,818,677 | 4/1989 | Hay-Kaufman et al. | 436/810 |
| 4,833,087 | 5/1989 | Hinckley | 435/287 |
| 4,859,603 | 8/1989 | Dole et al. | 435/287 |
| 4,895,706 | 1/1990 | Root et al. | 422/102 |
| 4,956,302 | 9/1990 | Gordon et al. | 436/161 |
| 4,960,692 | 10/1990 | Lentrichia et al. | 436/518 |

FOREIGN PATENT DOCUMENTS

0131934 1/1985 European Pat. Off. .
0200381 11/1986 European Pat. Off. .
2245797 3/1973 Fed. Rep. of Germany .

OTHER PUBLICATIONS

H. R. Schroeder, et al., Immunochemiluminometric Assay for Hepatitis B. Surgace Antigen, Clin. Chem. 27(8):1378-1384 (1984).
J. Kang, et al., Clin. Chem. 32(9):1682-1686 (1986).

Primary Examiner—Ester L. Kepplinger
Assistant Examiner—Christopher L. Chin
Attorney, Agent, or Firm—Frank S. Ungemach; Priscilla E. Porembski

[57] ABSTRACT

A method for performing a microparticle diagnostic assay in a device having a shallow sample well for receiving a sample and reagents for forming a reaction mixture, a read well positioned adjacent to said sample well and separated from said sample well by a wall which is constructed and arranged such that when wash fluid is injected into said sample well, sample and reaction mixtures are washed from said shallow sample well, over the wall and into said read well. The steps of the method comprise forming microparticle analyte complexes in said shallow sample well; washing said microparticle analyte complexes from said shallow sample well over the wall and into said read well where a fibrous matrix retains and immobilizes said microparticle analyte complexes; adding to said read well an indicator substance capable of forming an assay signal when said microparticle analyte complexes are present; and detecting said assay signal produced by said indicator substance.

14 Claims, 1 Drawing Sheet

METHODS FOR PERFORMING A SOLID-PHASE IMMUNOASSAY

This is a division of application Ser. No. 07/184,726, filed Apr. 22, 1988.

BACKGROUND OF THE INVENTION

The present invention is directed toward a disposable device suitable for use in an automated solid phase immunoassay. The device is designed to have two wells, one in which a sample material can be treated with reagents to perform a solid phase assay and another in which the results of that assay can be read. The reaction mixture is transferred from the sample well to the read well by a non-contact means using jets of fluid to move the reactants between the two wells.

Techniques for performing an immunoassay are generally well known in the art. For example, conventional enzyme immunoassay procedures involve a series of steps wherein an analyte in a sample material is initially bound to a corresponding antigen or antibody reagent. A second antigen or antibody is then introduced into the sample which has been labeled or conjugated with an enzyme or other substance capable of detection when treated with an additional suitable indicator reagent such as a chromogen or dye to produce a signal which is then read to indicate the absence or presence of the antigen or antibody in the sample.

Solid-phase immunoassay procedures are preferred over other diagnostic methods because of their safety, ease of use, specificity and sensitivity. Moreover, when employing a solid-phase immunoassay procedure, the result is easily observed by instruments which increases the accuracy of the procedure.

One form of a conventional solid-phase immunoassay is a "sandwich assay" which involves contacting a test sample suspected of containing an antibody or antigen with a substantially solid inert plastic or glass bead or other support material which can be coated with a protein or another substance capable of binding the antigen or antibody to the surface of the support. After the antibody or antigen is bound to the support material it is treated with a second antigen or antibody, which is conjugated with an enzyme, a fluorophore or a chemiluminescent label. The second antigen or antibody then becomes bound to the corresponding antibody or antigen on the support. Following one or more washing steps to remove any unbound material in an enzyme immunoassay, an indicator substance, for example, a chromogenic substrate, is added which reacts with the enzyme to produce a color chance. The color chance can be observed visually or more preferably by an instrument to indicate the presence or absence of an antibody or antigen in the sample. For solid phase fluorescence or chemiluminescence immunoassays, fluorescent labeled moieties can be monitored using excitation at an appropriate wavelength, while chemiluminescent labeled antigens or antibodies can be followed after reaction by chemically activating the chemiluminescent labels to generate light which can be detected by photometric means.

Many procedures and apparatus have been designed to perform solid-phase immunoassays. U.S. Pat. No. 4,632,901 discloses an apparatus having a porous filter containing a bound receptor for completing an analyte. In this apparatus an absorbent material is positioned below the porous filter to assist the fluid sample in flowing through the filter. A labeled antibody is then added to the porous filter to detect the presence or absence of the analyte.

In another approach, European Patent Application No. 0131934 discloses an assay device having a plurality of aligned adjacent reaction wells located on its top surface which empty through a filter membrane located above a waste reservoir. A solid phase fluorescent immunoassay reaction mixture is placed in the well and drawn through the membrane by applying reduced pressure to the waste reservoir to separate a solid-phase reaction product from a liquid-phase reaction product so that the solid-phase reaction product can be observed. This approach, however, has a serious limitation. Sample and microparticle incubation takes place in the same reaction well which can lead to non-specific binding of conjugates to the membrane filter contributing to the background of the assay and limits its sensitivity.

Other methods for performing a solid-phase enzyme immunoassay are disclosed in U.S. Pat. Nos. 4,587,102, and 4,552,839, and European Patent Application 0200381. These references generally disclose procedures for employing particles having a receptor to bind an analyte which is subsequently labeled and deposited on a matrix or other support system. The particle complex is treated with an indicator substance to indicate the presence or absence of an analyte.

While many immunoassay procedures and devices have proved useful, better procedures and devices are continually being sought to improve reliability, efficiency and sensitivity. The present invention provides all these improvements.

SUMMARY OF THE INVENTION

In one aspect, the present invention is directed toward a device suitable for performing an automated solid phase diagnostic assay. The ability to perform an automated assay contributes to increased reliability and efficiency.

The device of the present invention comprises a shallow sample well for receiving a sample material and a read well for retaining and immobilizing a microparticle, analyte complex. The device is designed to allow for the transfer of the sample and reagent reaction mixture from the shallow sample well to the read well without physically contacting the reaction mixture with a pipette or other transfer means. Thus contamination of the assay and apparatus is avoided which increases the sensitivity and accuracy of the assay. The transfer is conducted by effectively washing the reaction mixture from the first shallow sample well into a read well via a communicating passage means. This is achieved by washing the reaction mixture from the shallow sample well into the read well by injecting wash solution into the shallow sample well with a series of nozzles at high speed. The nozzles are directed at a specific angle to the shallow sample well. Separating the read well from the sample well decreases the possibility of nonspecific binding of the conjugate in the read well and improves assay sensitivity.

The read well has an entrance port, which is the terminus of the communicating passage means and a means for holding a quantity reacted sample and reagent mixtures positioned over a fibrous matrix which retains and immobilizes microparticle analyte complexes. The fibrous matrix is composed of fibers having an average spatial separation greater than the average diameter of the microparticles. Preferably the average fiber spatial separation is greater than 10 microns.

The read well may further comprise means for enhancing the flow of sample and assay reaction mixtures through the fibrous matrix such as vacuum or an absorbent material positioned below the fibrous matrix.

The present invention also provides various methods for performing a solid phase assay in the device. One method for performing a sandwich immunoassay in accordance with the invention comprises the following steps:

a) incubating the sample material with an analyte specific conjugate in the shallow sample well to form an analyte/conjugate complex;

b) adding microparticles having an average diameter smaller than the average spatial separation of the fibers forming the fibrous matrix to the sample well and then washing the analyte/conjugate complex into the read well to form a microparticle, analyte/conjugate complex;

c) adding additional wash solution to he read well to further wash the microparticle analyte/conjugate complex into the fibrous matrix where it is retained and immobilized;

d) adding a substance capable of producing a signal in the presence of the microparticle analyte/conjugate complex to the fibrous matrix; and e) detecting the signal produced.

Alternatively, step a) can be performed by simultaneously adding the microparticle, sample and analyte specific conjugate in the shallow sample well and then washing the mixture into the read well. In another alternative method, step b) can be performed by contacting the analyte/conjugate complex with microparticles in the shallow sample well to form a microparticle analyte/conjugate complex and then washing 'his complex into the read well.

In yet another embodiment step a) can be performed by incubating a sample with the microparticles in the shallow sample well and then washing the microparticle analyte complex formed into the read well. Alternatively, step b) can be performed by incubating a microparticle analyte complex with an analyte specific conjugate to form a microparticle analyte/conjugate complex, which is washed into the read well.

The disposable device can also be employed to conduct competitive assays. A competitive assay comprises incubating a sample and microparticles with an enzyme labeled antigen in the shallow sample well, washing the reaction mixture into the read well, adding a substrate to the read well and detecting the product formed.

DETAILED DESCRIPTION OF THE INVENTION

The present invention is directed toward a device and methods for performing a solid-phase immunoassay with the device. The device is disposable and is suitable for use with an apparatus having programmed instructions and means for injecting a wash solution to transfer the assay reaction mixture to a read well and for optically reading the results of the assay. The present invention also provides for a method of transferring reaction mixture from sample well to read well without physically contacting the reaction mixture with a pipette or other transfer means. The present invention further provides various methods for performing a solid-phase assay employing the disposable device.

The device is designed to be employed in a variety of solid-phase diagnostic assays such as sandwich or competitive binding assays. Further the device is designed so that it can be used for fluorescence, chemilumenescence, or colorimetric detection methods.

The device is molded to have at least two wells, a shallow sample well for receiving a sample which communicates by a passage means with a read well for detecting the results of the assay procedure. Preferably, the device is molded of styrene, acrylonitrile butadiene-styrene, polycarbonate or some other moldable material which is substantially inert to the assay procedure.

Samples which can be assayed by the device include biological fluids such as whole blood, spinal fluid, urine, serum, and plasma. It is also envisioned that other fluid samples of a nonbiological nature can be analyzed using the disposable device. The sample is placed either manually or mechanically into the shallow sample well and reacted (hereinafter described) and after an appropriate time washed into the read well where the results of the assay are monitored or detected. In a preferred embodiment the device is placed in a device tray or carousel designed to hold a plurality of devices for use in an automated analyzer. The carousel or the tray can be moved in such a manner that robotic means having multiple degrees of freedom can access each of the wells. The robotic means are eguipped with probes, pipettes or other transfer devices to aspirate, add, mix or transfer sample, reagents or other necessary substances to perform a solid-phase assay in the device wells. Preferably, robotic means direct wash solutions from appropriately oriented nozzles into the shallow sample well to affect transfer of the reaction mixtures.

Figure 1:
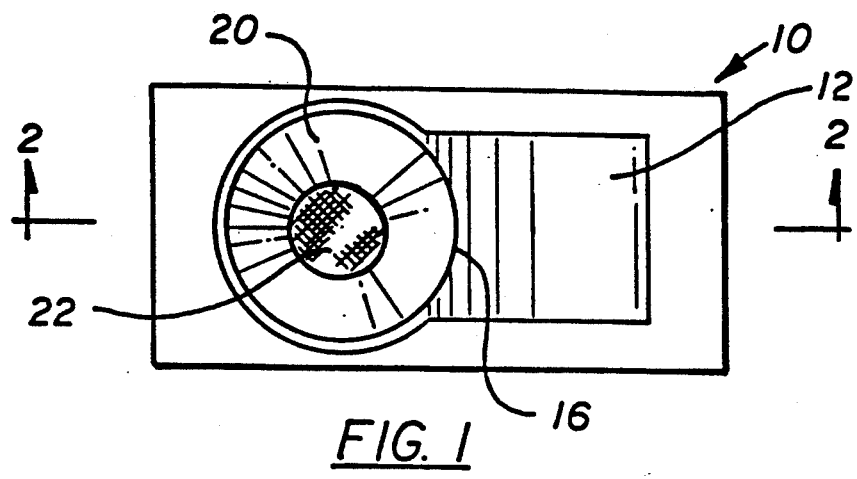
FIG. 1 is a top plane view for one embodiment of the diagnostic device.
Figure 2:
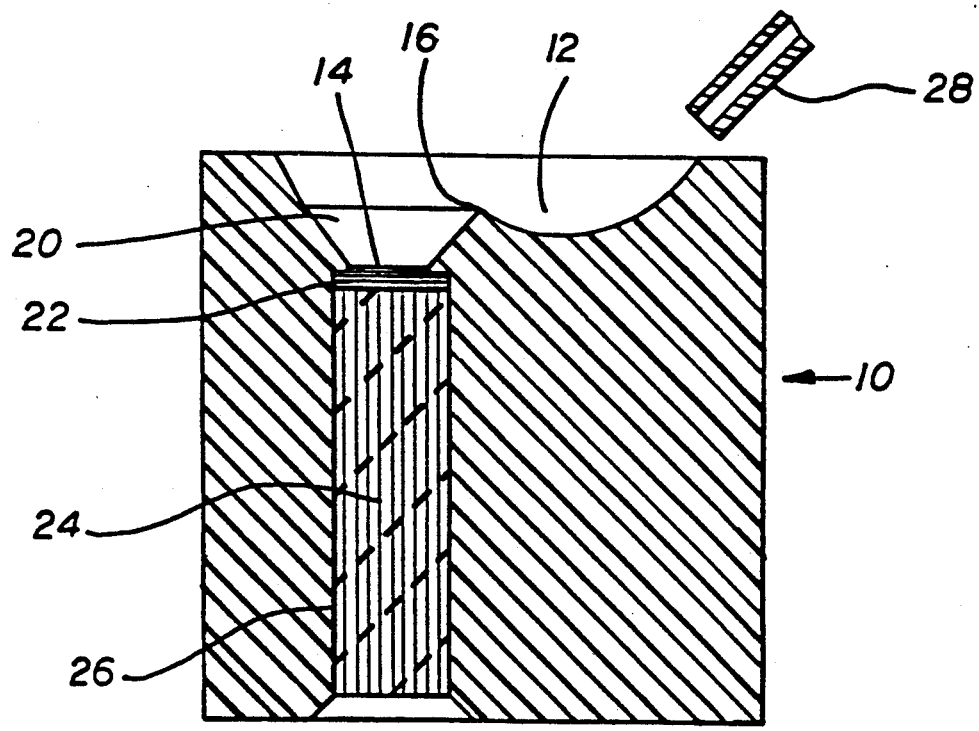
FIG. 2 is a side view in crosssection of the diagnostic device of FIG. 1.

In one embodiment, the device 10 is shown in FIGS. 1 and 2. The device as shown consists of a shallow sample well 12 and a read well 14 having fibrous and absorbent materials positioned therein. The shallow sample well 12 can be generally spherical, cylindrical, toroidal, or any complex curvature in shape. The largest radius of curvature of the shallow sample well is along the axis connecting the sample well to the well. The dimensions of the shallow sample well 12 are chosen to maximize the volume of reaction mixture that can be incubated in the well without having a steep fluid exit angle. A high fluid exit angle requires high wash solution injection speeds which may cause the reaction mixture to overshoot the read well. Conversely, a low exit angle can lead to self-transfer or spillage of reaction mixture into the read well. Choice of dimensions and their relationship to fluid properties can be easily calculated by those skilled in the art.

The read well 14 is located at a position on the device 10 so that when it is placed in a carousel or array format it can be readily scanned by an optical means to read the formation of an assay signal. After the assay is performed the device can be removed from the carousel or array tray and disposed.

The shallow sample well 12 as shown in FIGS. 1 and 2 is positioned in the device 10 so as to simplify the washing of sample and reagent reaction mixtures from the sample well 12 through a communicating passage means 16 to the read well by automated means. The wash solution is ejected from the nozzle(s) 28 as depicted in FIG. 2 for illustrative purposes.

Transfer takes place by injecting a wash fluid at the side of the shallow sample well 12, farthest from the read well 14. Nozzle(s) 28 are positioned close to the surface of the sample well 12 to inject wash solution. The solution is injected into the shallow sample well 12 at a small angle to the tangent of the surface of the well at its region of intersection with the surface of the reaction mixture. The angle between the direction of wash solution injection and the tangent of the well surface at its intersection with the reaction mixture surface is generally kept below 45 degrees. Angles between 5 and 20 degrees are preferred.

Wash solution injection speeds into the shallow sample well 12 that are needed to affect transfer depend on the reaction mixture volume to be transferred. Slow wash solution injection speeds into the sample well 12 may lead to a partial transfer, which in turn necessitates a larger capacity for disposal of excess wash solution. At the other extreme, a high wash solution injection speed into the shallow sample well 12 can cause the reaction mixture to overshoot the read well 14 and introduce the possibility of reaction mixture or wash solution splashing back toward the injector nozzles and contaminating them. Therefore, depth and curvature of the shallow sample well 12, the communicating passage means 16 exit angle and injection speed of wash solution are dependent on the total assay volume to be incubated in sample well 12 in order to achieve the desired binding reaction under the constraints of the assay conditions. Those skilled in the art of fluid dynamics can easily calculate and optimize these dimensions without departing from the spirit of this invention.

An alternative preferred way to transfer reaction mixture from shallow sample well 12 into read well 14 is to use a combination of pressurized air and wash solution nozzles and simultaneously activating them to affect transfer.

The read well 14 generally comprises the terminus of the communicating passage means 16, which acts as an entrance port and holding means 20, and a porous fibrous matrix 22. Means for evacuating the communicating passage means of reaction mixture and wash solution can also be provided such as by vacuum or absorbent means positioned below the porous fibrous matrix 22. The sample well 12, the communicating passage means 16 and holding means 20 can be a molded portion of the device or preferably a funnel-like structure which is press-fitted or sonic welded into the orifice of the read well 14. The holding means 20 is designed with sloping sides which contact the upper surface of the fibrous matrix 22 and is sized to hold a sufficient amount of sample, reagents and transfer solution to satisfy the requirements of the particular assay being performed. While the holding means 20 can be any color a darker color or preferably black may be chosen to decrease background interference with the optics system.

The porous fibrous matrix 22 is a thin, disk like material positioned below the communicating passage means 16 and holding means 20 to retain and immobilize a microparticle complex from which an assay signal can be read. The phrase "retain and immobilize" means that the microparticles, while upon the fibers of the material, are not capable of substantial movement to positions elsewhere within the material, (i.e., to other fibers), and cannot be removed completely from the material without destroying the material.

The pore size or spatial separation of the fibers comprising the fibrous matrix 22 is essential to the overall performance of the solid-phase immunoassay contemplated by the present invention. Specifically, the spatial separation of the fibers must be larger than the diameter of the microparticles employed in the assay. This is to assure that even after the microparticles are immobilized on the fibers adequate void areas will exist to assure the proper flow of reagents and sample through the fibrous matrix. Despite the large spatial separation of the fibers, the microparticles do not pass through the fibrous matrix; instead, the microparticles are immobilized upon the fibers themselves. The immobilization is not by entrapment, filtration or covalent bonding. The exact interaction between the microparticles and the fibers is not completely understood; however, the interaction that does result has been found to be especially appropriate for the performance of the subject solid-phase immunoassay methods. That is, after the microparticles are deposited on the fibrous matrix, the matrix is not blocked but instead remains porous. As used herein "porous" means that the matrix is and remains a material into which fluids can flow and can easily pass through.

The fibrous material of the present invention can be chosen from any of a variety of materials such as glass, cellulose, nylon or other natural or synthetic fibrous material well known to those skilled in the art. One suitable material is H&V Product No. HC4111 glass fiber filter paper, which has a nominal thickness of 0.055 inches and is commercially available from Hollingsworth and Vose Co., East Walpole, Massachusetts. The thickness of such a material is not critical, and is a matter of choice for one skilled in the art, largely based upon the properties of the sample being assayed, such as its fluidity.

The microparticles employed to perform the solid phase immunoassay are selected to have an average diameter smaller than the average spatial separation of the fibers that form the fibrous matrix. Also, the size of the microparticles employed is preferably small enough such that they are suspendable in water or sucrose to facilitate their coating with an antibody or antigen. The average individual size of the microparticles which can meet both of the above requirements is from about 0.1 to about 10 microns, more preferably from about 0.1 to about 5 microns in diameter. The microparticles can be selected from any suitable type of particulate material such as polystyrene, polymethylacrylate, polypropylene, latex, polytetrafluoroethylene, polyacrylonitrile, polycarbonate or similar materials.

Uncoated microparticles can be employed for binding some analytes but in many situations the particles are coated with a substance for binding an analyte, e.g., antibody or antigen, or a combination thereof.

In one preferred embodiment the fibrous matrix 22 is positioned against the holding means 20 and above an absorbent material 24. The absorbent material 24 can be any shape however for ease of construction it can be generally cylindrical or flat. It generally functions to facilitate the transportation of fluid through the fibrous matrix 22. The absorbent material 24 can be any moisture or fluid-retaining material which effectively retains fluid passing through the fibrous matrix 22. Generally the absorbent material 24 can be composed of natural or synthetic fibers or other materials capable of absorbing fluid, i.e. cotton, cellulose acetate glass fibers, and synthetic or natural sponge. Preferably an absorbent material is employed where the fibers run perpendicular to the lower surface of the fibrous matrix to provide a capillary action to assist in drawing fluid through the fibrous matrix.

The absorbent material 24 is generally positioned below the fibrous matrix 22 to absorb any reagent or sample that flows through the fibrous matrix 22. One preferred manner for positioning the absorbent material 24 is to place it in intimate contact with the lower surface of the porous, fibrous matrix 22. This contact assures rapid transportation of the reaction fluids through the fibrous matrix 22.

The absorbent material 24 can be surrounded by a paper or cellophane wrapper 26 as shown in FIG. 2. The primary function of the wrapper 26 is to facilitate installation of the absorbent material under the read well 14 and to prevent damage to the absorbent material 24 itself. The device 10 can include molded features to properly position the absorbent material 24 under the read well 14.

As an example, molded fins extending from the interior side walls of the device 10 which are wider at their base than at their tops (not depicted in FIGS. 1 or 2) can be employed. The fins would effectively force the absorbent material 24 up into the fibrous matrix 22 which in turn firmly positions the fibrous matrix 22 against the holding means 20. An alternative design would be a molded spike located at the base of the device 10. The spike forces the absorbent material 24 into intimate contact with the lower surface of the fibrous matrix 22.

The transfer and treatment of a sample with reagents in the device is preferably but not necessarily accomplished by robotic means. Robotic arms can supply the necessary reagents by various transferring means communicating with reagent containers located external to the device and associated carousel. Most importantly, the robotic arms can position a pipetting or jet means for directing a stream of wash solution into the shallow sample well 12 or otherwise flood the shallow sample well 12 to wash the assay reaction mixture through the communicating passage means 16 into the read well 14. This procedure can be easily accomplished manually by pipetting means or by merely pouring a wash solution into the shallow sample well 12. This particular feature of the device 10 prevents contamination of the automated apparatus or pipetting means as well as the assay reaction mixture. Also, because a pipette tip never touches the assay mixtures the pipette never needs to be washed to prevent cross contamination of other assays.

In an automated solid phase assay procedure the robotics are controlled by associated electronic and computer hardware and software designed to perform predetermined steps for a particular assay. Methods for performing a solid-phase immunoassay with the device require the use of microparticles which complex with the analyte sought to be assayed. Whether the solid-phase assay performed is a sandwich assay or a competitive assay, the results of the test are dependent upon the ability of the microparticles to become retained and immobilized on the fibrous matrix.

For illustration purposes the following procedures are provided:

In one form of a sandwich assay method a sample is added to the shallow sample well and the device is placed in a carousel or other holder means designed to hold a plurality of devices. Steps (a) through (e) may be performed by a microprocessor controlled automated instrument or manually as follows:

(a) an analyte specific conjugate is added to the shallow sample well containing a sample to form a mixture which is incubated for a sufficient time to allow any analyte present to complex with the analyte specific conjugate;

(b) microparticles are added to the mixture to form a microparticle, analyte/conjugate complex; alternatively, the analyte/conjugate complex can be washed into the read well to which microparticles have been previously or simultaneously added;

(c) the incubated microparticle, analyte/conjugate complex is washed into the receiving port of the read well and washed with a suitable buffer or water to transport the complex into the porous fibrous matrix;

(d) an indicator substance capable of producing a color change or other detectable signal in the presence of the microparticle analyte/conjugate complex is added to the read well; and (e) the assay signal is detected by optical means as a function of the presence or amount of analyte in the sample.

In a variation of the above procedure, steps (a) and (b), i.e., formation of analyte/conjugate complex and formation of microparticle, analyte/conjugate complex, respectively, can be performed simultaneously by adding the microparticles, sample and analyte specific conjugate to the shallow sample well and incubated. The complex is then washed into the read well.

In the final step (e), detection of the signal produced in the read well varies with the type of label used. Thus for an enzyme labeled antigens or antibodies, a substrate solution is added in the read well and the product formed is detected by color development or generation of a fluorescent signal. For fluorophore labeled antigen or antibodies, direct excitation of fluorophore and detection of spontaneous or time resolved fluorescence signal is used. In the case of chemiluminescent labeled antigens or antibodies, detecting is achieved by chemically activating the chemiluminescent label and monitoring generated light. In all these methods of detection either the total integrated signal over a period of time or the rate of change in signal over the observation period can be used to establish a standard curve for the assay and determine the concentration of the analyte.

In another version of a solid-phase sandwich assay procedure the automated or manual steps can be performed as follows:

(a) a sample and microparticles are mixed together in the sample well to form a complex of the microparticle and analyte;

(b) the microparticle analyte complex is treated with an analyte specific conjugate and incubated to form a microparticle analyte/conjugate complex (alternatively steps (a) and (b) can be performed simultaneously by adding sample, microparticles and an analyte specific conjugate to the sample well, incubating and washing the complex formed into the read well);

(c) the complex is then transported into the fibrous matrix by applying a wash of a suitable buffer or water;

(d) an indicator substance capable of producing a signal in the presence of the microparticle analyte/conjugate complex is added to the read well to form a assay signal;

(e) the assay signal is detected by optical means as a function of the presence or amount of analyte in the sample.

In yet another solid-phase immunoassay approach the disposable device can be employed to perform a competitive binding assay. The automated or manual steps are as follows:

(a) a sample is added to a known amount of labeled antigen and microparticles capable of binding a suspect antigen to form a mixture in the sample well;

(b) the mixture is washed into the read well where the microparticles become bound to the fibrous matrix;

(c) the fibrous matrix is washed to remove unbound antigen;

(d) an indicator substance is added to the read well to form an assay signal in the presence of the labeled antigen; and (e) the assay signal is detected by optical means as a function of the presence or amount of analyte in the sample.

It should be apparent that many variations of the above steps can be designed to form the microparticle, analyte/conjugate, substrate complex which can be detected by optical means on the porous, fibrous matrix. Generally the sandwich or competitive assay procedure and the choice of an analyte specific conjugate, and indicator substance are known to those skilled in the art and therefore are not discussed in great detail here. Instead, the present invention is directed toward the device described above and in a preferred embodiment to the device which is suitable for the automated performance of a solid-phase immunoassay process on a microprocessor-controlled automated instrument.

Another embodiment of the present invention is to assemble a plurality of the shallow sample well 12, communicating passage means 16 and read well 14 into a square or a rectangular array. Each read well element has a separate porous fibrous matrix 22 and either a separate absorbent material element 24 or a common absorbent material pad or layers of absorbent material pads. It can also be assembled in such a way that individual absorbent material elements 24 are in intimate contact with the fibrous matrix 22 on one end and with a common absorbent layer on the other end. Any of the absorbent material configurations can be chosen to enhance diffusion of fluids away from the porous fibrous matrix 22. The array assembly is useful where a high throughout instrument is desired.

Following are examples of solid-phase assays performed with the subject device.

EXAMPLE 1

The following is an example of a competitive binding assay for Hepatites B anticore antibody.

Microparticles were prepared with carboxylated polystyrene latex particles, to which recombinant DNA Hepatites B core antigen had been chemically bound using an EDAC coupling procedure. The amount of microparticles used was 18 ug/test. Samples were anticore negative control and anticore positive control from a commercial enzyme immunoassay kit core panel controls #6 and #7.

A device similar to that described in the embodiments of this invention was constructed. Sample and reagents were incubated in the shallow reaction well. Wash solution was injected from an assembly of three adjacent nozzles connected via a manifold to a stepper motor controlled pump. Nozzles were directed at an angle of 13° to the tangent to the shallow well surface at its point of intersection with reaction mixture surface. In this geometry nozzles were at a 60° angle to the horizontal plane. Wash solution was injected in the manifold at the rate of 1700 uL per second. The exit angle of the fluid was 28°.

Three procedures were followed:

Procedure A: Control Method I

1. Pipet 100 uL of sample, 50 uL acridinium labeled anticore antibodies and 50 uL of antigen coated latex particles into a polystyrene reaction tray well.

2. Seal reaction tray with adhesive paper tape and incubate in a water bath at 40° for one hour.

3. Using a manual pipet, transfer all of reaction mixture onto the fibrous matrix in the read well of the device of the subject invention. The device was contained in an assay having 16 devices in total arranged side-by-side in two rows of eight (2 by 8).

4. Wash the fibrous matrix with three aliquots 100 uL each of 0.1% Tween-20.

5. Insert array into a chemiluminescence breadboard reader. Trigger and measure the chemiluminescent signal off the captured microparticles on the porous fibrous matrix.

Procedure B: Control Method II

1. Pipet 100 uL of sample, 50 uL acridinium labeled anticore antibodies and 50 uL of antigen coated latex particles into the shallow reaction well of 2 by 8 array of the device of the subject invention.

2. Cover the array with a metal cover that is bent to fit over it leaving a small air gap.

3. Incubate for one hour in an air oven at 40° C.

4. Using a manual pipet, transfer 150 uL of reaction mixture onto the fibrous matrix of read well.

5. Wash matrix with three 100 uL aliquots of 0.1% Tween-20.

6. Read the chemiluminescent signal off the matrix using the same procedure as described in A.

Procedure C: Method of the Subject Invention

1. Pipet 100 uL of sample, 50 uL acridinium labeled anticore antibodies and 50 uL of antigen coated latex particles into shallow well of a 2 by 8 array of the subject device.

2. Cover the array with a metal cover that is bent to fit over it leaving a small air gap.

3. Incubate for one hour in an air oven at 40° c.

4. Remove from oven. Transfer and wash the reaction mixture from shallow reaction well through the passage means onto the porous fibrous matrix of read well. Transfer was affected by injecting two pulses of 300 uL each of 0.1% Tween-20 into the flow rate of 1560 uL per second from three 0.020 ID nozzles. The average velocity from each nozzle is 2.6 m/sec.

5. Read the chemiluminecent signal off the matrix using the same procedure as described in A and B.

In all procedures a negative control sample, a positive control sample and two sensitivity panel members were run. One of the panel members was positive and the other was negative. They were chosen to straddle the gray zone area in a typical enzyme immunoassay procedure.

Cut-off was determined by calculating the percent inhibition of signal.

% Inhibition =

$$\frac{100 \text{ (Mean of Negative Control} - \text{Mean of Sample)}}{\text{(Mean of Negative Control} - \text{Mean of Positive Control)}}$$

A % inhibition of 60% and higher was taken as positive and a % inhibition less than 60% was assigned as negative.

Data are tabulated in Table 1. Percent inhibition figures indicate the validity of the fluidics transfer and show that transfer of reaction mixture and washing of porous matrix was affected using the method and device of the present invention

TABLE 1

| | Hepatites B Anticore Antibody Assay | | | | | |
|---|---|---|---|---|---|---|
| | Procedure A Control I | | Procedure B Control II | | Procedure C Subject Invention | |
| Sample | Total Counts | % Inhibition | Total Counts | % Inhibition | Total Counts | % Inhibition |
| Negative Control | 105,192 | | 96,720 | | 96,755 | |
| Positive Control | 6,793 | | 6,617 | | 7,152 | |
| Panel #6 | 33,735 | 73 | 27,582 | 77 | 30,084 | 74 |
| Panel #7 | 51,644 | 47 | 48,667 | 54 | 44,108 | 59 |

We claim:

1. A method for performing a solid-phase diagnostic assay in a device having a shallow well for receiving a sample and reagents for forming a reaction mixture which produces a detectable component corresponding to an analyte in the sample; a read well positioned adjacent to said sample well comprising (a) an entrance port and wash receiving means for receiving a quantity of sample and assay reagents from said sample well; (b) a fibrous matrix for retaining and immobilizing said detectable components, said fibrous matrix positioned below and in fluid communication with said wash receiving means; and (c) means positioned below said fibrous matrix for assisting the flow of sample and assay reagents through said fibrous matrix; and said shallow sample well and said wash receiving means are separated by a wall which is constructed and arranged such that when wash fluid is injected into said sample well, sample and reaction mixtures are washed from said shallow sample well, over and into said read well; the steps of the method comprising:
    (a) incubating a sample with an analyte specific conjugate in said sample well to form an analyte/conjugate complex;
    (b) simultaneously adding microparticles, such microparticles having an average diameter smaller than the average spatial separation of the fibers forming sad fibrous matrix and having an analyte binding substance immobilized thereon, to form a microparticle, analyte/conjugate complex and washing said microparticle, analyte/conjugate complex from said shallow sample well, over and into said read well where said fibrous matrix retains and immobilizes said microparticle, analyte/conjugate complex;
    (c) adding a wash solution to said read well;
    (d) adding to said read well an indicator substance capable of forming an assay signal in the presence of said microparticle, analyte/conjugate complex; and
    (e) detecting said assay signal produced by said indicator substance in step (d) as a function of the presence or amount of analyte in said sample.

2. The method of claim 1 wherein step (b) is performed by first contacting said analyte/conjugate complex with said micropraticles, incubating the mixture to form a micropraticle, analyte/conjugate complex and then washing said microparticle, analyte/conjugate complex over and into said read well.

3. The method of claim 1, wherein steps (a) and (b) are performed simultaneously by incubating a sample, microparticles and an analyte specific conjugate in said shallow sample well and then washing the microparticle, analyte/conjugate complex over and into said read well.

4. The method of claim 1, wherein said microparticles are spherical polymeric particles.

5. The method of claim 1, wherein said microparticles have an average diameter from about 0.1 to about 10 microns.

6. The method of claim 1, wherein step (e) consists of performing a series of rapid readings to determine a rate for the complexing of said indicator substance with said microparticle, analyte/conjugate complex.

7. A method for performing a solid-phase diagnostic assay in a device having a shallow sample well for receiving a sample and reagents for forming a reaction mixture which produces a detectable component corresponding to an analyte in the sample; a read well positioned adjacent to said sample well comprising (a) an entrance port and wash receiving means for receiving a quantity of sample and assay reagents from said sample well; (b) a fibrous matrix for retaining and immobilizing said detectable components, said fibrous matrix positioned below and in fluid communication with said wash receiving means; and (c) means positioned below said fibrous matrix for assisting the flow of sample and assay reagents through said fibrous matrix; and said shallow sample well and said wash receiving means are separated by a wall which is constructed and arranged such that when wash fluid is injected into said sample well, sample and reaction mixtures are washed from said shallow sample well, over and into said read well; the steps of said method comprising;
    (a) adding a sample to said shallow sample well in the presence of microparticles which have an average diameter smaller than the average spatial separation of the fibers forming said fibrous matrix and have an analyte binding substance immobilized thereon, and incubating to form a microparticle, analyte complex;
    (b) adding to said shallow sample well and thereby to said microparticle, analyte complex an analyte specific conjugate and incubating the mixture to form a microparticle analyte/conjugate complex;
    (c) washing said microparticle, analyte/conjugate complex over and into said read well;
    (d) adding to said read well an indicator substance capable of forming an assay signal in the presence of said microparticle, analyte/conjugate complex; and
    (e) detecting said assay signal produced by said indicator substance in step (d) as a function of the presence or amount of analyte in said sample.

8. The method of claim 7, wherein said microparticles are spherical polymeric particles.

9. The method of claim 7, wherein said microparticles have an average diameter from about 0.1 to about 10 microns.

10. The method of claim 7, wherein said step (e) consists of performing a series of rapid readings to determine a rate for the complexing of said indicator substance with said microparticle, analyte/conjugate complex.

11. A method for performing a solid-phase diagnostic assay in a device having a shallow sample well for receiving a sample and reagents of forming a reaction mixture which produces a detectable component corresponding to an analyte in the sample; a read well positioned adjacent to said sample well comprising (a) an entrance port and wash receiving means for receiving a quantity of sample and assay reagents from said sample well; (b) a fibrous matrix for retaining and immobilizing said detectable components, said fibrous matrix positioned below and in fluid communication with said wash receiving means; and (c) means positioned below said fibrous matrix for assisting the flow of sample and assay reagents through said fibrous matrix; and said shallow sample well and said wash receiving means are separated by a wall which is constructed and arranged such that when wash fluid is injected into said sample well, sample and reaction mixtures are washed from said shallow sample well, over and into said read well; the steps of said method comprising:
- (a) treating a sample with a labeled antigen and microparticles, such microparticles having an average diameter smaller than the average spatial separation of the fibers forming said fibrous matrix and having an antigen binding substance immobilized thereon and capable of binding an antigen to form a reaction mixture thereof in said shallow sample well.
- (b) washing said reaction mixture over and into said read well whereby said microparticles become retained and immobilized on said fibrous matrix;
- (c) washing said fibrous matrix to remove any unbound antigen;
- (d) applying an indicator substance to said reaction well to form an assay signal with said labeled antigen; and
- (e) detecting said assay signal produced by said indicator substance in step (d) as a function of the presence or amount of said antigen in said sample.

12. The method of claim 11, wherein said microparticles are spherical polymeric particles.

13. The method of claim 11, wherein said microparticles have an average diameter from about 0.1 to about 10 microns.

14. A method for performing a solid-phase diagnostic assay in a device having a shallow sample well for receiving a sample and reagents for forming a reaction mixture which produces a detectable component corresponding to an analyte in the sample; a read well positioned adjacent to said sample well comprising (a) an entrance port and wash receiving means for receiving a quantity of sample and assay reagents from said sample well; (b) a fibrous matrix for retaining and immobilizing said detectable components, sad fibrous matrix positioned below and in fluid communication with said wash receiving means; and (c) means positioned below said fibrous matrix for assisting the flow of sample and assay reagents through said fibrous matrix; and said shallow sample well and said wash receiving means are separated by a wall which is constructed and arranged such that when wash fluid is injected into said sample well, sample and reaction mixtures are washed from said shallow sample well, over the wall and into said read well; the steps of said method comprising:
- (a) adding a sample to said shallow sample well in the presence of microparticles which have an average diameter smaller than the average spatial separation of the fibers forming said fibrous matrix and have an analyte binding substance immobilized thereon, and incubating to form a microparticle, analyte complex;
- (b) washing said microparticle, analyte complex over and into said read well;
- (c) adding an analyte specific conjugate to said read well to form a microparticle analyte/conjugate complex;
- (d) adding to said read well an indicator substance capable of forming an assay signal in the presence of said microparticle, analyte/conjugate complex; and
- (e) detecting said assay signal produced by said indicator substance in step (d) as a function of the presence or amount of analyte in said sample.

* * * * *